United States Patent [19]

Wu et al.

[11] 4,246,909
[45] Jan. 27, 1981

[54] DISPOSABLE URETHRAL CATHETER ASSEMBLY

[75] Inventors: Yeongchi Wu, Darien; Roger A. Erber, Mt. Prospect, both of Ill.

[73] Assignee: Illinois Tool Works Inc., Chicago, Ill.

[21] Appl. No.: 947,961

[22] Filed: Oct. 5, 1978

[51] Int. Cl.³ .............................................. A61M 1/00
[52] U.S. Cl. .................................... 128/762; 128/767; 128/768; 128/275; 128/DIG. 24; 206/364
[58] Field of Search ............. 128/275, 294, 295, 34 R, 128/DIG. 9, DIG. 24, 760, 762, 763, 765, 766, 767, 768, 770; 206/364, 438, 571

[56] References Cited

U.S. PATENT DOCUMENTS

| | | |
|---|---|---|
| 2,853,069 | 9/1958 | Beacham et al. ............ 128/DIG. 24 |
| 2,856,932 | 10/1958 | Griffitts ....................... 128/DIG. 24 |
| 3,189,252 | 6/1965 | Miller ........................... 128/DIG. 24 |
| 3,683,928 | 8/1972 | Kuntz ............................... 128/349 R |
| 3,838,691 | 10/1974 | Paludan ................................. 128/275 |
| 3,937,213 | 2/1976 | McDonald ........................... 128/275 |
| 4,000,649 | 1/1977 | Hanifl ................................... 128/762 |
| 4,091,922 | 5/1978 | Egler .................................... 206/364 |
| 4,204,527 | 5/1980 | Wu et al. .............................. 128/762 |

FOREIGN PATENT DOCUMENTS 2601180  7/1976  Fed. Rep. of Germany ........... 128/275

OTHER PUBLICATIONS

Research Disclosure, Aug. 1973, "Female Incontinance Device and Support Garment," pp. 42–43.

*Primary Examiner*—Robert W. Michell
*Assistant Examiner*—J. L. Kruter
*Attorney, Agent, or Firm*—Thomas W. Buckman; Jack R. Halvorsen

[57] ABSTRACT

A disposable urethral catheter assembly includes a flexible bag in which a number of chambers are defined by barriers. In an upper chamber, a catheter is contained in a sterile environment. When the catheter is inserted through the urethra into the bladder, the fluid flows into the bag through the upper chamber and into a lower sample chamber, excess fluid being collected in the upper chamber. After catheterization, a one-piece element which provides a sealable passageway through the first barrier between the upper and lower chamber can be readily closed by manipulation through the wall of the bag and thus isolate the sample in the lower chamber. The upper chamber, its contents and the catheter are separated from the sealed lower chamber and discarded. The lower sample chamber which provides a sterile environment for its contents can then be sent to a laboratory for analysis and culture.

10 Claims, No Drawings

U.S. Patent   Jan. 27, 1981   4,246,909
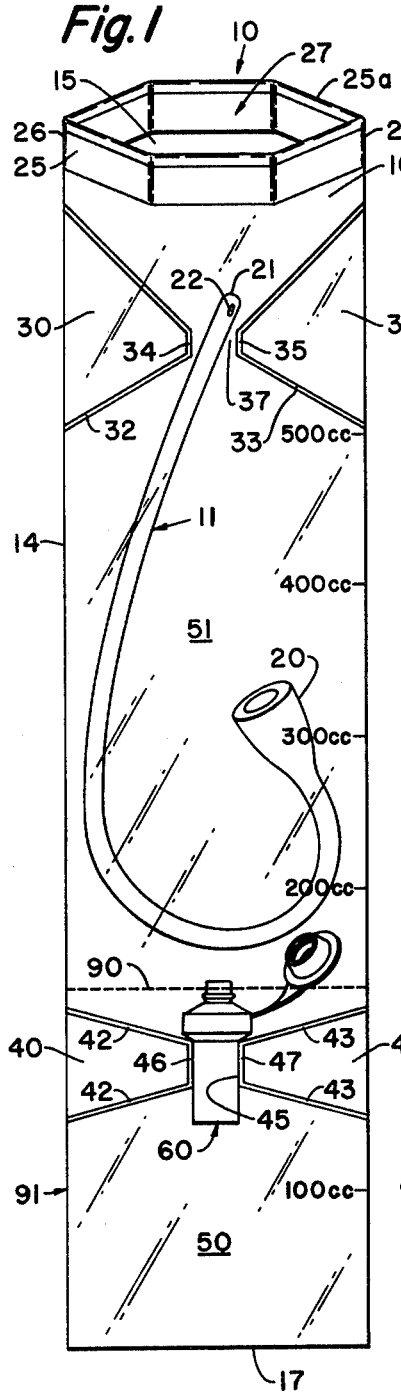
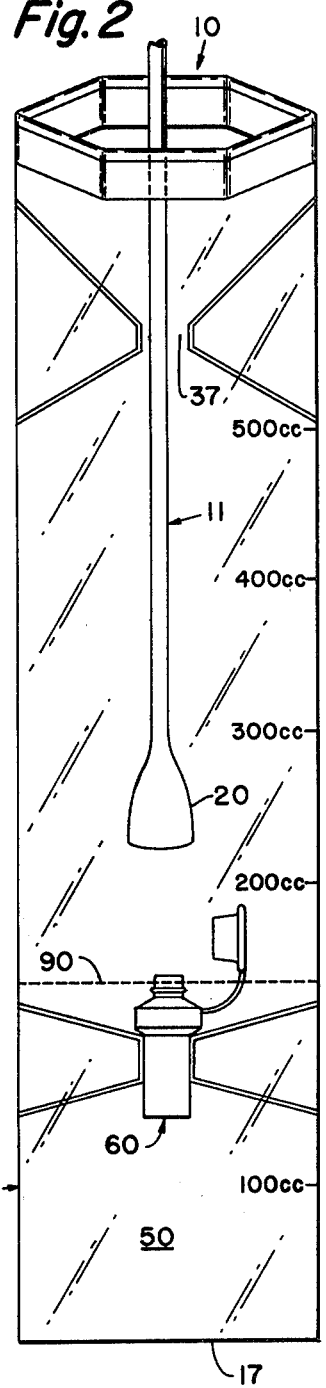
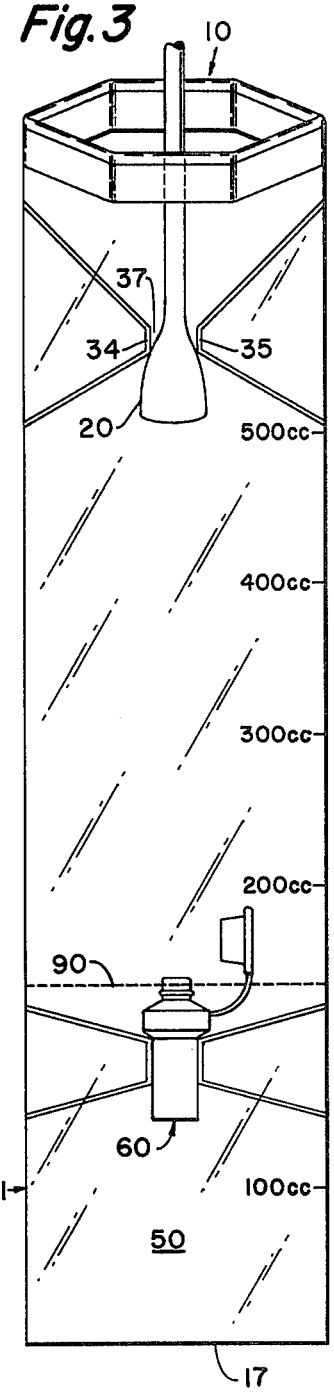
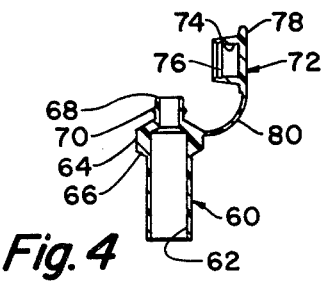
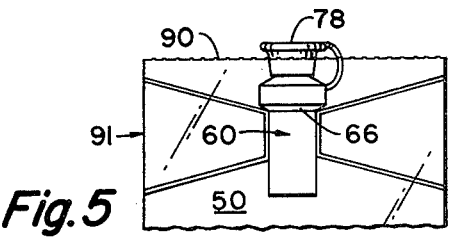

DISPOSABLE URETHRAL CATHETER ASSEMBLY

BACKGROUND OF THE INVENTION

This invention relates generally to fluid collectors for use with catheters and related apparatus, and more particularly concerns a catheter fluid collector device which more or less automatically isolates a fluid sample for later laboratory study, including urinalysis and culture and sensitivity tests.

Many victims of paralysis are unable to voluntarily evacuate their bladder. These persons must be catherterized periodically in order to remove accumulating body waste fluids.

A number of non-surgical and semi-surgical techniques and related devices have been offered to perform this catheterization. For male patients this procedure in general involves aseptically preparing the penis, and then inserting a catheter into the urethra, while maintaining sterile technique, until the eye of the catheter reaches and communicates with the bladder. Urine then flows through the catheter and can be directed into a collection container or disposal device.

If a urine specimen is required for medical analysis, the urine flow from the catheter is directed into a specimen collection container until an adequate sample is collected; remaining portions of the urine flow are then directed back into the disposal structure. When the bladder has been emptied and the procedure completed, the catheter is removed and disposed of, and the specimen container is sealed and sent to a laboratory for microbiological and biochemical studies.

At least some of these techniques and their associated implements offer the dangers of urethra contamination during procedure preparation, catheter contamination during handling, and specimen contamination during specimen container filling, sealing and emptying. Many of the techniques and associated apparatus must be performed in a semi-surgical setting; they cannot be conveniently performed by the patient himself while he is alone and in a semi-private washroom or other location.

Additionally, when collector bags or receptacles are provided, some catheterization apparatus permit inadvertent removal of the catheter from the collector, thus presenting the possibility of accidental spillage and attendant mess. Such as occurrence can cause discomfort and even humiliation to the patient.

It is accordingly the general object of the present invention to provide a urine collector which is handy and safe to use, and which more or less automatically containerizes a urine sample for laboratory analysis.

It is a more specific object of the invention to provide a urine collector and catheter device which minimizes the danger of catheter contamination during catheter insertion into the urethra. An associated object is to provide such a collector and catheter which encourages and maximizes the maintenance of sterile technique. An ancillary object is to provide such a collector and catheter which permits catheter insertion without the catheter being directly touched or handled at any time.

Another object of the invention is to provide a urine collector and catheter which minimizes the risk of urine sample contamination from outside sources. A related object is to provide such a collector and catheter which more or less automatically segregates or defines and encapsulates or containerizes a urine sample. A related object is to provide such a device in which the sealed urine sample is contained in a handy chamber, and which can be poured and otherwise manipulated in the laboratory with relative ease.

Yet another object is to provide a collector and a catheter which could be used by the patient himself when he is alone in a washroom or a relatively private area.

A further object of the invention is to provide such a collector and catheter which can be manufactured, packaged, and commercially offered at an attractive cost.

Still another object is to provide such a collector and catheter which can be used with relative ease even by relatively inexperienced personnel. An associated object is to provide such a collector and a catheter which can be used by the patient himself with a minimum of instruction to thereby reduce the professional time and final medical expense.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 1 is an elevational view of the novel collector and catheter as they appear when ready for use;

FIG. 2 is an elevational view similar to FIG. 1 showing the catheter and collector as they appear when the catheter is being inserted into the urethra;

FIG. 3 is an elevational view similar to FIGS. 1 and 2 and showing the collector and catheter as they can appear when the catheter has been relatively fully inserted and is about to deliver a quantity of fluid to the collector;

FIG. 4 is a sectional elevational view of the one-piece element forming the sealable passageway through the barrier defining the two chambers in the bag; and FIG. 5 is an elevational view of a collector first chamber which has been filled with fluid, sealed by closure of the one-piece element, separated from the balance of the bag and ready for removal to a laboratory for analysis.

DETAILED DESCRIPTION

While the invention will be described in connection with a preferred embodiment and procedure, it will be understood that it is not intended to limit the invention to this embodiment or procedure. On the contrary, it is intended to cover all alternatives, modifications and equivalents as may be included within the spirit and scope of the invention and defined by the appended claims. For example, this collector device and procedure can be used, with suitable minor modifications, by female as well as male patients.

Turning first to FIG. 1, there is shown the novel collector 10 and catheter 11 embodying the present invention. Here the collector takes the form of a transparent flexible bag 14 made of a suitable polymeric film such as any of the appropriate polyolefins, polystyrenes or the like. The bag can be of an elongated form, as illustrated, and is defined by two folded or otherwise opposed material layer films 15 and 16 sealed at a bottom 17 and may also be sealed at the top 25a with a suitable tear seal. Such sealing of top 25a can be used in the event the collector is not packaged in a secondary sterile container or envelope. It is contemplated that the bag interior will be rendered sterile by appropriate operations during manufacture.

The catheter 11 can be considered to comprise an elongated hollow tube 19 terminating at one end in an enlarged or bulbous discharge end 20. At an opposite tip 21, an eye or perforation 22 communicates with the hollow tube interior, as is well known in the art of urethra catheters. The catheter, too, is rendered sterile during manufacturing.

After manufacturing production and prior to use, the catheter 11 is carried in a sterile environment. To this end, the bag 14 is provided with a closure top 25. If desired, a resilient member within the closure top 25 can be biased into an open position from its normally closed position by squeezing opposite edges 26 toward each other to provide an irregular, hollow, polygonal opening and chamber 27 for accommodating the head of a male penis. This top chamber 27 is at least partly defined by two upper chevrons 30 and 31 formed within and upon the bag, as by heat sealing narrow bands 32 and 33 of one bag side 15 against the opposite bag side 16.

In use, the urethra orifice and head of the penis is asepticized. The bag top 25 is then opened by tearing seal 25a and squeezing edges 26, thereby exposing and forming the top chamber 27. A suitable lubricant is added to top chamber 27 and the penis glans is inserted into chamber 27 until it contacts chevrons 30 and 31 thereby orienting and aligning the urethra with the opening 37. The bag 14 and catheter 11 are then manipulated so as to extend the catheter 11 out from the top of the bag, as illustrated in FIG. 2. In accordance with one aspect of the invention, this procedure eliminates the need for directly touching the catheter 11, for the bag opening 27 is adapted to be brought over the penis head. Since the interior of the opening 27 is aseptic, catheterization procedure sterility is encouraged.

It will be noted that these upper chevrons 30 and 31 extend toward one another, but terminate at truncations 34 and 35, respectively, which define a restricted opening 37 through which the catheter tube 19 extends. To discourage inadvertent catheter removal in accordance with another aspect of the invention, the opening 37 is reduced in size relative to the enlarged catheter bulbous end 20 whereby end 20 cannot be inadvertently pulled through, as particularly illustrated in FIG. 3. When male patients use the novel device, the catheter can be gripped through the bag with the forefinger and thumb of one hand while the penis is held against the chevrons 30 and 31 inside the bag top cavity 27. The patient or user eases the catheter tube 19 into the urethra orifice and into the urethra itself with succeeding gripping and releasing motions, allowing the plastic bag 14 to first corrugate and then to relax into its original position after each movement. In this way, the catheter is inserted into the urethra until the catheter tube opening or eye 22 enters the bladder and urine begins flowing into the bag. Urine flow is permitted until a substantial portion of the bladder has been evacuated. When catherization has been completed, or when the maximum acceptable volume has been received in the bag, the patient or user removes the catheter and bag in one outward motion.

In accordance with yet another aspect of the invention, a urine sample of convenient volume for laboratory analysis is more or less automatically collected by this device and procedure. To this end, two lower chevrons or barriers 40 and 41 are formed within and upon the bag, as by heat sealing the bags sides 15 and 16 to one another along outwardly diverging lines 42 and 43 respectively. A relatively narrow opening 45 is defined between two opposed heat sealed lines 46 and 47. To maintain a free passage through the barrier formed by chevrons 40 and 41 there is provided a one-piece sealable tubular element 60. In prior art collector units, such as shown in U.S. Pat. No. 4,204,527 issued May 27, 1980, a moveable cannula plug was located in the lower chamber 50. It was necessary to manipulate such a plug within the bag to align it with the narrow opening 45 and then move the plug axially to seal the passageway. This was found to be a difficult and often distasteful operation due to spillage of liquid from the upper reservoir 51. On many occasions the manipulation operation resulted in pinholes being formed in the bag resulting in leakage from the bag and contamination of the asceptic conditions.

To overcome these difficulties the present invention utilizes a one-piece tubular element 60 having a through bore 62, an enlarged portion 64 forming a shoulder 66 and a reduced necked-down portion 68, the latter, in this embodiment, having an annular ring 70 located intermediate the extremities of portion 68. Integrally attached to element 60 is a sealing cap 72 having a closed bore 74 with an annular groove 76, the bore and groove being complimentary to portion 68 and ring 70. The closed end of cap 72 may include a lateral flange 78 to which is attached one end of a hinge-like strap 80 which is connected at the opposite end to the enlarged portion 64 of element 60.

During fabrication of the collector 10, the element 60 is positioned and immobilized by the heat sealing of chevrons 40 and 41 with the shoulder 66 formed by enlarged portion 64 locating element 60 relative to the diverging lines 42 and 43 and further acting as a reactant to the force of the liquid pressure or head formed when reservoir 51 is filled as well as when cap 72 is moved into closed sealing relation with portion 64.

In the operation of the collector 10 the tubular element 60 with the cap in its open position permits a predetermined quantity of fluid to flow into the specimen reservoir, in this embodiment the lower or first chamber 50. When the first chamber 50 is filled, additional fluid accumulates in a relatively upper or second chamber 51. The total volume of fluid material collected can be determined with reasonable accuracy by a volumetric measurement scale marked upon the bag when the bag is held in a vertical position, as indicated in FIGS. 1 through 3.

If a specimen is desired the cap 72 is manipulated through the bag into a closed position, as seen in FIG. 5, the top or second chamber 51, the catheter 11, and other portions of the device can be discarded, in further accordance with the invention. To do this, the entire device 10 is preferably removed to a disposal area, where the fluid in the second or top chamber 51 is emptied. The patient or attendant then removes the catheter 11 and top portion of the bag 14, as by tearing or cutting along a convenient sever line 90 which can be marked upon the bag. The lower portion 91 of the device, including the filled and sealed first chamber 50, can then be transmitted to the laboratory for urine analysis and culture, sensitivity tests together with desired identifying data, such as the patient's name and any hospital room number.

In the laboratory, a laboratory techician removes the cap portion 72 from the element 60. After the fluid sample is dispensed and tests have been completed, the device lower portion 91 and any unused fluid can also be discarded, thereby eliminating any need to undertake costly re-sterilization procedures.

I claim:

1. A fluid collector including a urethral catheter for delivering a quantity of liquid from a human body, and a flexible bag containing the catheter prior to catheter use, said bag including first barrier means defining at least a first chamber capable of containing a predetermined volume of liquid and a second chamber capable of containing the liquid delivered from said body in excess of the liquid deposited in said first chamber, said collector further including a permanently positioned one-piece means defining a sealable passageway through said first barrier to provide controlled egress between said first and second chambers, said one-piece means including a pass-through tubular element having an enlargement adjacent one end thereof to provide shoulder means for engagement with said barrier means to prevent movement through said barrier into said first chamber and to maintain said element in substantially fixed relation to said barrier, said enlargement is reduced inwardly in diameter at said one end to form a neck means, and a cap means integrally connected by a hinge-like member to said element and adapted to sealingly cooperate with said neck means to close egress through said tubular element.

2. A fluid collector according to claim 1 wherein said bag is an elongated rectangle formed of a transparent flexible polymeric film.

3. A fluid collector according to claim 1 wherein said first barrier means includes two opposed chevron formations formed in and on said bag.

4. A fluid collector according to claim 3 wherein said chevron formations each include a chevron defined by line portions of said bag heat sealed to an adjacent but opposed portion of the bag.

5. A fluid collector according to claim 4 wherein said chevrons take the form of opposed trapezoids.

6. A fluid collector according to claim 1 wherein said hinge-like member connecting said cap to said tubular element is a strap means which permits manipulation of said cap from an open to a closed position through the closed walls of said bag, whereby a specimen sample of the liquid from said body can be retained in said first chamber while the liquid in said second chamber is disposed of generally after withdrawal of said catheter from said body.

7. A fluid collector according to claim 1 further including a second barrier means separating said second chamber at least partially from an adjacent portion of said bag spaced from said first chamber, said second barrier means having a central passageway adapted to permit passage therethrough of at least part of said catheter.

8. A fluid collector according to claim 7 wherein said catheter is equipped with stop means which cooperates with said second barrier means substantially preventing complete withdrawal of the catheter from the second chamber.

9. A fluid collector according to claim 8 wherein said catheter stop means comprises an enlarged catheter end for abutment against said second barrier means when withdrawal of said catheter from said chamber is attempted.

10. A fluid collector including, in combination, a volume-calibrated, internally sterile elongated bag and a urethral catheter contained therein, the lower portion of said bag including a barrier formed by opposed heat sealed chevrons forming a fluid specimen reservoir of predetermined volume, a one-piece tubular element having a moveable integral sealing closure at one end, said element permanently positioned and retained between said chevrons to provide controlable access to said reservoir, said bag further including a second set of heat sealed opposed chevrons adjacent the top of said bag to define a channel communicating between the ambient open end of said bag and a second reservoir defined by said bag between the first and second sets of chevrons, said catheter initially being located in said second reservoir and adapted to be extended through said channel during catheterization.

* * * * *